(12) United States Patent
Liu et al.

(10) Patent No.: US 8,193,762 B2
(45) Date of Patent: Jun. 5, 2012

(54) BATTERY CHARGING APPARATUS OF A WIRELESS DIGITAL X-RAY DETECTOR

(75) Inventors: James Zhengshe Liu, Glenview, IL (US); Gilbert Wu, Waukesha, WI (US); Meghan Fox, Milwaukee, WI (US)

(73) Assignee: General Electric Company, Schenectady, NY (US)

(*) Notice: Subject to any disclaimer, the term of this patent is extended or adjusted under 35 U.S.C. 154(b) by 401 days.

(21) Appl. No.: 12/177,877

(22) Filed: Jul. 22, 2008

(65) Prior Publication Data

US 2010/0019720 A1 Jan. 28, 2010

(51) Int. Cl.
*H02J 7/00* (2006.01)
(52) U.S. Cl. .......................... 320/107; 378/177
(58) Field of Classification Search .................. 320/112, 320/115; 378/167, 177–180
See application file for complete search history.

(56) References Cited

U.S. PATENT DOCUMENTS

| | | | |
|---|---|---|---|
| 3,705,984 A | 12/1972 | Westenberger | |
| 4,414,683 A | 11/1983 | Robinson | |
| 5,022,065 A | 6/1991 | Wijkstrom | |
| 5,226,068 A | 7/1993 | Strawder | |
| 5,473,664 A | 12/1995 | Strawder | |
| 5,479,471 A | 12/1995 | Buckland | |
| 5,563,926 A | 10/1996 | Brotzman | |
| 5,640,439 A | 6/1997 | Strawder | |
| 5,708,840 A | 1/1998 | Kikinis et al. | |
| 5,729,587 A | 3/1998 | Betz | |
| 5,844,961 A | 12/1998 | McEvoy et al. | |
| 5,867,553 A | 2/1999 | Gordon et al. | |
| 5,877,501 A | 3/1999 | Ivan et al. | |
| 6,017,149 A | 1/2000 | Strawder | |
| 6,044,131 A | 3/2000 | McEvoy et al. | |
| 6,143,970 A | 11/2000 | Kowzan | |
| 6,337,712 B1 | 1/2002 | Shiota et al. | |
| 6,440,072 B1 | 8/2002 | Schuman et al. | |
| 6,475,146 B1 | 11/2002 | Frelburger et al. | |
| 6,833,867 B1 | 12/2004 | Anderson | |
| 7,022,075 B2 | 4/2006 | Grunwald et al. | |
| 7,270,477 B1 | 9/2007 | Kari | |
| 7,342,998 B2 | 3/2008 | Kump et al. | |
| 7,696,722 B2* | 4/2010 | Utschig et al. | 320/114 |
| 7,715,187 B2* | 5/2010 | Hotelling et al. | 361/679.41 |
| 2003/0078072 A1 | 4/2003 | Serceki et al. | |
| 2005/0135564 A1 | 6/2005 | Dippl et al. | |

(Continued)

OTHER PUBLICATIONS

Broadcom press release # 659800, "Broadcom, HP and Linksys Make Wi-Fi Installation as Easy as Pushing a Button," printed Dec. 16, 2005.

(Continued)

*Primary Examiner* — Ramy Ramadan
(74) *Attorney, Agent, or Firm* — William Baxter, Esq.; Michael G. Smith, Esq.

(57) ABSTRACT

Systems, methods and apparatus are provided through which in some implementations a portable wireless digital X-ray detector includes a battery electrically coupled to at least one external electrical conductor. In some implementations, the external electrical conductor is mounted flush to an outside of a housing of the portable wireless digital X-ray detector. In some implementations, the external electrical conductor plate includes only hypoallergenic materials. In some implementations, the battery is fixed mounted in the portable wireless digital X-ray detector. In some implementations docking detector receptacle at least one external electrical conductor in a pocket of the docking detector receptacle.

22 Claims, 10 Drawing Sheets

U.S. PATENT DOCUMENTS

| | | |
|---|---|---|
| 2005/0136892 A1 | 6/2005 | Oesterling et al. |
| 2005/0197093 A1 | 9/2005 | Wiklof et al. |
| 2006/0054822 A1* | 3/2006 | Tsuchino .................. 250/336.1 |
| 2006/0061323 A1* | 3/2006 | Cheng et al. .................. 320/108 |
| 2006/0070384 A1 | 4/2006 | Ertel |
| 2006/0108977 A1* | 5/2006 | Kagermeier et al. ......... 320/108 |
| 2006/0213845 A1 | 9/2006 | Utshig |
| 2007/0004980 A1 | 1/2007 | Warner et al. |
| 2007/0140424 A1 | 6/2007 | Serceki |
| 2007/0180046 A1 | 8/2007 | Cheung et al. |
| 2007/0269010 A1 | 11/2007 | Turner |
| 2008/0144777 A1 | 6/2008 | Wilson |

OTHER PUBLICATIONS

Broadcom press release #682849, "Broadcom makes Wi-Fi Phone Installation as Easy as Pushing a Button," printed Dec. 16, 2005.

* cited by examiner

BATTERY CHARGING APPARATUS OF A WIRELESS DIGITAL X-RAY DETECTOR

RELATED APPLICATION

This application is related to copending U.S. application Ser. No. 12/169,201 filed Jul. 8, 2008 entitled "MULTI-PURPOSE DOCKING APPARATUS OF DIGITAL X-RAY DETECTOR."

FIELD

This invention relates generally to power supply of medical image devices, and more particularly to power supply of portable wireless digital X-ray detectors.

BACKGROUND

Digital X-ray detectors have electronic sensors of X-ray electromagnetic energy. The digital X-ray detectors are often referred to as solid-state X-ray detectors.

One type of conventional digital X-ray detector includes an array of pixels composed of switches as FETs (field effect transistors) and light detectors such as photodiodes, the pixels being constructed of amorphous silicon, over which Cesium Iodide (CsI) is deposited. CsI absorbs the X-rays and converts them to light, which is then detected by the photodiodes. The photodiode acts as a capacitor and will store charge. Initialization of the detector takes place prior to an X-ray exposure, when during the course of "scrubbing" the detector, each photodiode is charged to a known voltage. The detector is then exposed to X-rays which are absorbed by the CsI. Light that is emitted in proportion to the X-ray flux then partially discharges the photodiode. After the conclusion of the exposure, the voltage on the photodiode is restored to the initial voltage. The amount of charge required to restore the initial voltage on the photodiode is measured, which becomes a measure of the X-ray dose integrated by the pixel during the length of the exposure. The pixel array is arrayed in a flat panel. A motherboard includes readout electronics that control readout of the electrical charge from the panel.

Conventional portable digital X-ray detectors include a tether which connects to imaging systems and/or mobile digital X-ray imaging systems that provide electrical power to the portable digital X-ray detectors and exchange data between the portable digital X-ray detectors and the imaging systems and/or mobile digital X-ray imaging systems. The tether is cumbersome and prone to maintenance problems.

For the reasons stated above, and for other reasons stated below which will become apparent to those skilled in the art upon reading and understanding the present specification, there is a need in the art for a more convenient means of providing power to the portable wireless digital X-ray detectors.

BRIEF DESCRIPTION

The above-mentioned shortcomings, disadvantages and problems are addressed herein, which will be understood by reading and studying the following specification.

In one aspect, an apparatus includes a panel of a pixel array mounted inside a housing, a processor operably coupled to the panel, a battery electrically coupled to the processor, and at least one electrically conductive plate that is mounted flush to an outside of the housing, the plate including only hypoallergenic materials.

In another aspect, a portable wireless digital X-ray detector includes a panel of a pixel array mounted inside a housing, a processor operably coupled to the panel, and a battery that is fixedly mounted and unremovable in the housing and electrically coupled to the processor.

In yet another aspect, a portable wireless digital X-ray detector includes a panel of a pixel array mounted inside a housing, a processor operably coupled to the panel, a battery in the housing and electrically coupled to the processor, and a battery-charging indicator that is operable to indicate the amount of remaining battery power and if the battery is under charging. The, battery-charging indicator being the mounted on the housing and operably coupled to the processor.

In still another aspect, a portable wireless digital X-ray detector includes a panel of a pixel array mounted inside a housing, a processor operably coupled to the panel, a battery in the housing and electrically coupled to the processor, and a battery-status indicator that indicates amount of charge of the battery, the battery-status indicator being mounted on the housing and operably coupled to the processor.

In a further aspect, an apparatus includes a back plane and a pocket coupled to the back plane, the pocket having interior dimensions into which a portable digital X-ray detector fits snugly and the pocket having at least one electrical conductor mounted to the interior of the pocket.

In yet a further aspect, a docking detector receptacle includes a back plane, a pocket coupled to the back plane, the pocket has interior dimensions into which a portable digital X-ray detector fits snugly and the pocket has a plurality of electrically conductive plates that is mounted to the interior of the pocket, and at least one spring underneath each of the plurality of electrically conductive plates.

In still yet a further aspect, a docking detector receptacle includes a back plane, a pocket coupled to the back plane, the pocket having interior dimensions into which a portable digital X-ray detector fits snugly and the pocket having a plurality of electrically conductive plates that is mounted to the interior of the pocket, and at least one spring underneath each of the plurality of electrically conductive plates.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into two sections. In the first section, apparatus implementations are described. In the second section, a conclusion of the detailed description is provided.

Apparatus Implementations

Figure 1:
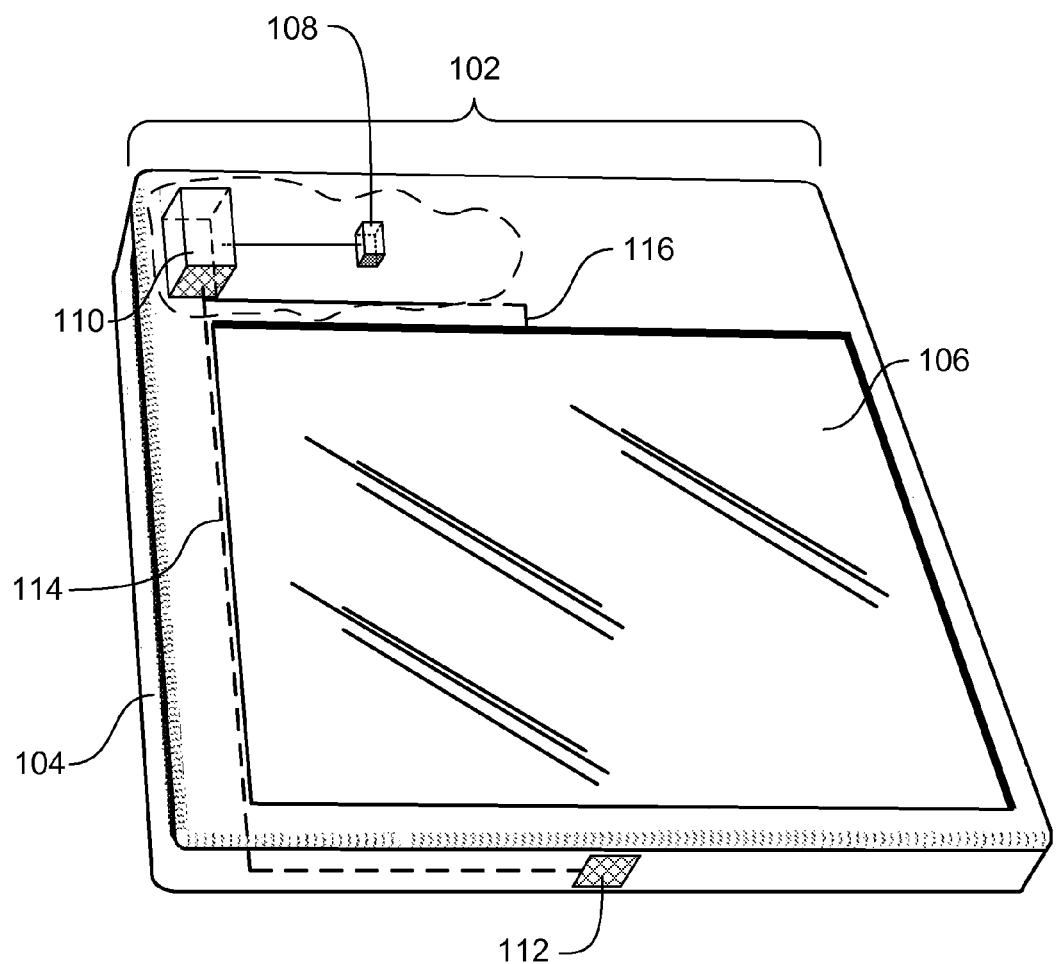
FIG. 1 is an isometric diagram of a portable wireless digital X-ray detector system having external electrical conductors.

FIG. 1 is an isometric diagram of a portable wireless digital X-ray detector system 100 having external electrical conductors. Portable wireless digital X-ray detector system 100 provides a convenient means of providing power to the portable wireless digital X-ray detectors.

Portable wireless digital X-ray detector system 100 includes a housing 102 that has an inside (not shown) and an outside 104. Portable wireless digital X-ray detector system 100 also includes a pixel array panel 106 that is mounted inside the housing 102. Portable wireless digital X-ray detector system 100 also includes a processor 108 that is operably coupled to the panel 106.

Portable wireless digital X-ray detector system 100 also includes a battery 110 or batteries that are electrically and operably coupled to the processor 108. In some implementations, the battery 110 can store about 30 watt-hours of electrical power. A battery 110 having 30 watt-hours of electrical power has a small physical profile and light weight, thus providing light weight to the portable wireless digital X-ray detector system 100. In some implementations, the battery 110 is fixedly mounted and unremovable in the housing 102, in which case the battery 110 is a permanent fixture of the portable wireless digital X-ray detector system 100. In some implementations, the battery 110 is removable. In this case, the removable battery 110 can be recharged in an X-ray system. Removable batteries can be swapped between the portable wireless digital X-ray detector system 100 in situations when one of the removable batteries is not charged.

Portable wireless digital X-ray detector system 100 also includes one or more electrical conductor(s) 112. In some implementations, such as shown in FIG. 1, the electrical conductor(s) 112 are electrically conductive plate(s). In other implementations shown in FIG. 6, the electrical conductor(s) 112 are pin(s).

In some implementations, the electrical conductor(s) 112 are electrically and operably coupled to the battery 110 through a charging circuit (not shown) and electrical path 114. The electrical path 114 provides electrical power to the battery 110 when electric power is applied to the electrical conductor(s) 112. The electric power can recharge the battery 110.

In some implementations, the read-out electronics (not shown) and panel 106 are electrically and operably coupled to the battery 110 through an electrical path 116. The electrical path 116 provides electrical power and/or signal communication to the read-out electronics and panel 106 from the battery 110. In other implementations, the battery 110 is a power source of every electrical component in the portable wireless digital X-ray detector 100, such as the panel 106, data modules (not shown), scan modules (not shown), and motherboard (not shown).

The electrical conductor(s) 112 provide a means through which the portable wireless digital X-ray detector system 100 can receive electrical power when the portable wireless digital X-ray detector system 100 is placed in a docking detector receptacle. Thus, the battery 110 of the portable wireless digital X-ray detector system 100 can be recharged during idle periods of the portable wireless digital X-ray detector system 100, which provides a convenient means of providing power to the portable wireless digital X-ray detector 100.

In some implementations, the electrical conductor(s) 112 include some hypoallergenic material(s), such as polyisobutene. The hypoallergenic material(s) are particularly beneficial to a portable wireless digital X-ray detector system 100 that may come in contact with a patient, or person, because the hypoallergenic material(s) reduces, if not eliminates, the possibility of the electrical conductor(s) 112 causing an allergic reaction in a patient or other person such as radiological technicians, nurses or physicians that may come into physical contact with the portable wireless digital X-ray detector system 100. In some implementations, the electrical conductor(s) include only hypoallergenic materials.

In some implementations, the electrical conductor(s) 112 are mounted flush to the outside 104 of the housing 102. The flush mounting of the electrical conductor(s) 112 is particularly beneficial to a portable wireless digital X-ray detector system 100 that may come in contact with a patient, or person, because the flush mounting reduces, if not eliminates, the possibility of edges of the electrical conductor(s) 112 catching on the skin or clothing of patients or other people such as radiological technicians, nurses or physicians, and possibly causing injury to the person or possibly acting as a deposit of human epidermis and/or blood that could be passed to a next person who comes in contact with the electrical conductor(s) 112, thus acting as a medium through which viruses and/or bacteria is transmitted from one person to another. Thus, the flush mounting of the electrical conductor(s) 112 prevents cross-contamination between people who have physical contact with the portable wireless digital X-ray detector system 100. In some implementations, the electrical conductor(s) 112 are mounted flush within a tolerance of 0.1 millimeters of the housing 102.

In some implementations, the electrical conductor(s) 112 have beveled edge(s) (not shown). The beveled edge(s) of the electrical conductor(s) 112 is particularly beneficial to a portable wireless digital X-ray detector system 100 that may come in contact with a patient, or person, because the beveled edge(s) reduces, if not eliminates, the possibility of edges of the electrical conductor(s) 112 catching on the skin or clothing of patients or other people such as radiological technicians, nurses or physicians, and possibly causing injury to the person or possibly acting as a deposit of human epidermis and/or blood that could be passed to the next person who comes in contact with the electrical conductor(s) 112, thus acting as a medium through which viruses and/or bacteria is transmitted from one person to another. Thus, the beveled edge(s) of the electrical conductor(s) 112 prevents cross-contamination between people who have physical contact with the portable wireless digital X-ray detector system 100.

In some implementations, a retractable cover (not shown) spans each of the electrical conductor(s) 112 to prevent dust and other contamination from coating the electrical conductor(s) 112. The retractable cover(s) help maintain sufficient electrical conductivity of the electrical conductor(s).

While the portable wireless digital X-ray detector system 100 is not limited to any particular housing 102, housing outside 104, pixel array panel 106, processor 108, battery 110, electrical conductor(s) 112 and electrical path 114, for sake of clarity a simplified housing 102, housing outside 104, pixel array panel 106, processor 108, battery 110, electrical conductor(s) 112 and electrical path 114 are described.

In the previous section, a system level overview of the operation of an implementation was described. In this section, the particular apparatus of such an implementation are described by reference to a series of diagrams.

Figure 2:
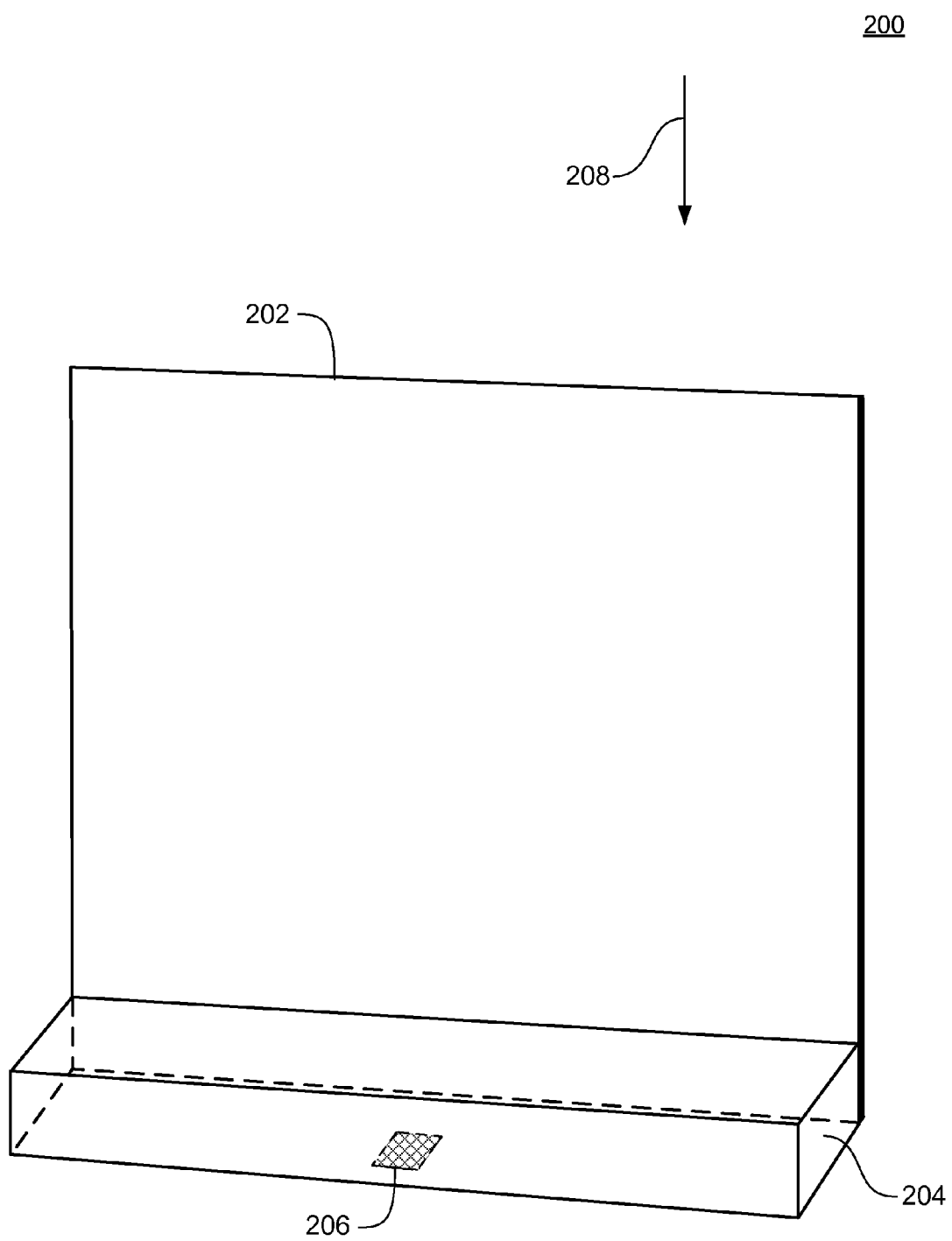
FIG. 2 is an isometric diagram of a docking detector receptacle 200 having electrical conductors.

FIG. 2 is an isometric diagram of a docking detector receptacle 200 having electrical conductors. Docking detector receptacle 200 provides a convenient means of providing power to portable wireless digital X-ray detectors.

Docking detector receptacle 200 includes a backplane 202 and a pocket 204 that is coupled to the backplane 202. The pocket 204 has interior dimensions into which a portable digital X-ray detector fits snugly. The pocket 204 is also referred to as a bin.

The pocket 204 includes one or more electrical conductor(s) 206 mounted to the interior of the pocket 204. The electrical conductor(s) 206 provide electrical power to a portable digital X-ray detector when electric power is applied to the electrical conductor(s) 206 and when the portable digital X-ray detector is placed 208 in the pocket 204.

In some implementations, the electrical conductor(s) 206 include some hypoallergenic material(s), such as polyisobutene. In some implementations, the electrical conductor(s) 206 include only hypoallergenic materials.

Figure 6:
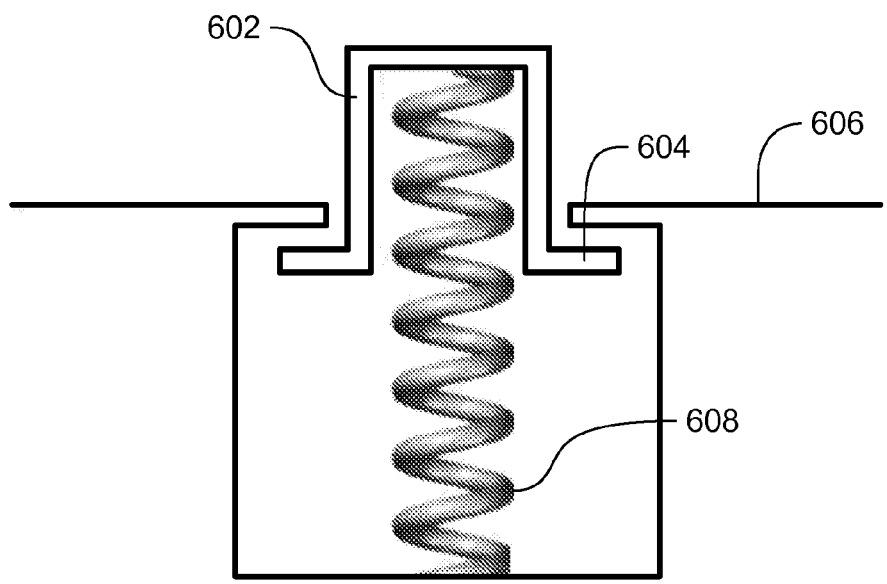
FIG. 6 is a cross section block diagram of an electrical conductor spring assembly.

In some implementations, the electrical conductor(s) 206 are mounted above flush to the interior of the pocket 204. Above flush is raised above the interior surface of the pocket. In some implementations, the electrical conductor(s) 206 include one or more spring(s) (not shown) underneath the electrical conductor(s) 206. The spring(s) have a tension force that holds the electrical conductor(s) 206 above flush to the interior of the pocket 204 when no force is applied against the electrical conductor(s) 206. The springs also have a force that holds the electrical conductor(s) 206 about flush to the interior of the pocket 204 when a full weight of a portable wireless digital X-ray detector is applied against the electrical conductor(s) 206. One implementation of the springs is shown in FIG. 6.

In some implementations, such as shown in FIG. 2, the electrical conductor(s) 206 are electrically conductive plate(s). In other implementations not shown, the electrical conductor(s) 206 are pin(s).

Figure 3:
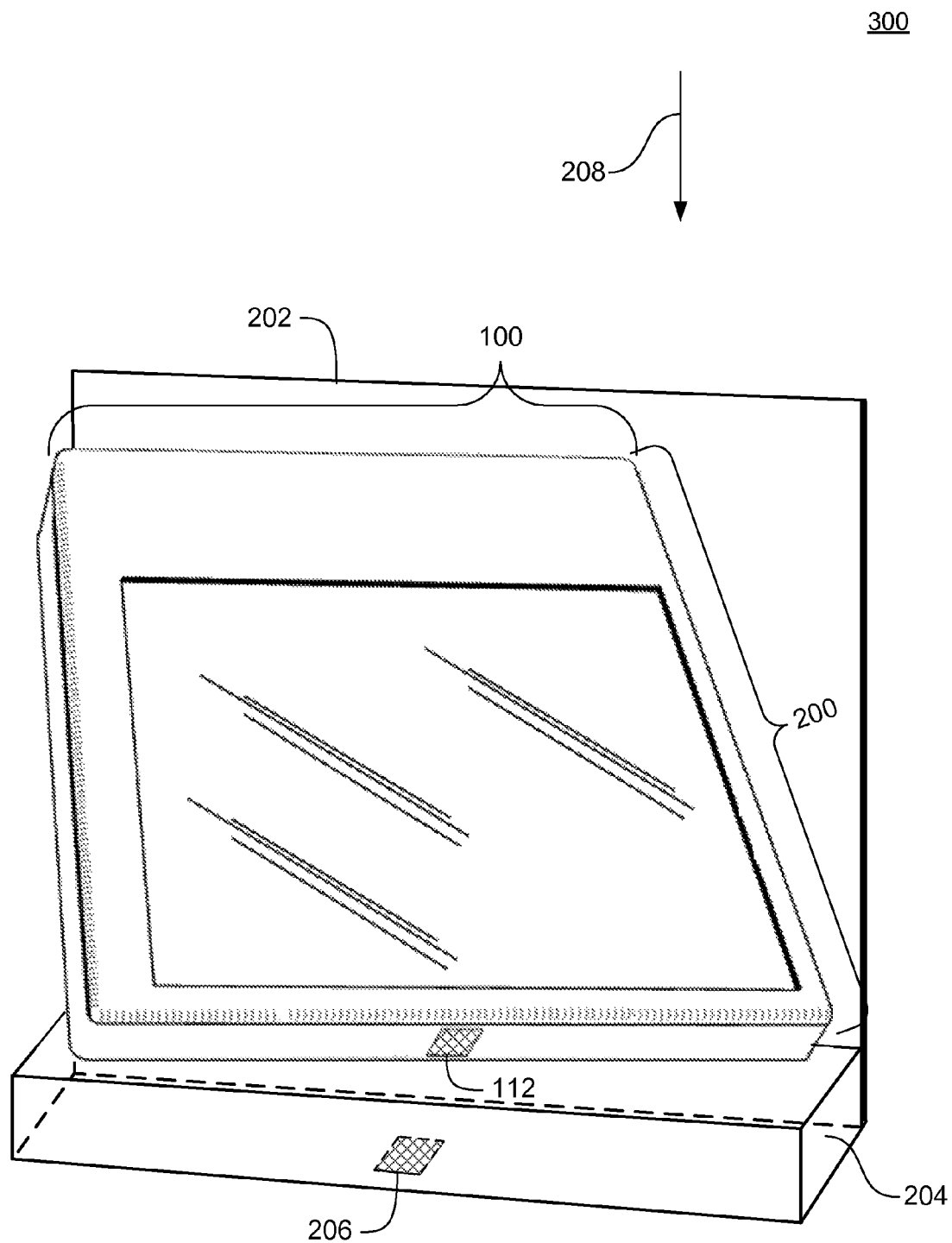
FIG. 3 is an isometric diagram of a portable wireless digital X-ray detector system and a docking detector receptacle having adjacent electrical conductors.

FIG. 3 is an isometric diagram of a portable wireless digital X-ray detector system and a docking detector receptacle having adjacent electrical conductors. The portable wireless digital X-ray detector system and docking detector receptacle of FIG. 3 provide a convenient means of providing power to the portable wireless digital X-ray detector from the docking detector receptacle.

The electrical conductors (112 and 206) of the portable wireless digital X-ray detector system 100 and the docking detector receptacle 200 are positioned at locations on the respective items that are adjacent or adjoining to each other when the portable wireless digital X-ray detector system 100 is placed in the pocket 204 of the docking detector receptacle 200. Each of the electrical conductor(s) on the housing of the portable wireless digital X-ray detector system 100 are located in a position on the housing that is adjacent to an electrical conductor in the pocket of the docking detector receptacle 200. The position of the electrical conductors provides physical and electrical contact between the portable wireless digital X-ray detector system 100 and the docking detector receptacle 200 when the portable wireless digital X-ray detector system 100 is placed in the pocket 204 of the docking detector receptacle 200. Thus an electrical path is created between the portable wireless digital X-ray detector system 100 and the docking detector receptacle 200 when the portable wireless digital X-ray detector system 100 is placed in the pocket 204 of the docking detector receptacle 200.

In some implementations, electrical conductor(s) 112 are located on the bottom of the housing of the portable wireless digital X-ray detector system 100, and the electrical conductor(s) 206 are located on the interior bottom of the pocket 204 of the docking detector receptacle 200, as shown in FIG. 3.

In some implementations that are not shown, electrical conductor(s) 112 are located on the side and/or the bottom of the housing of the portable wireless digital X-ray detector system 100, and the electrical conductor(s) 206 are located on the interior side and/or bottom of the pocket 204 of the docking detector receptacle 200.

Figure 4:
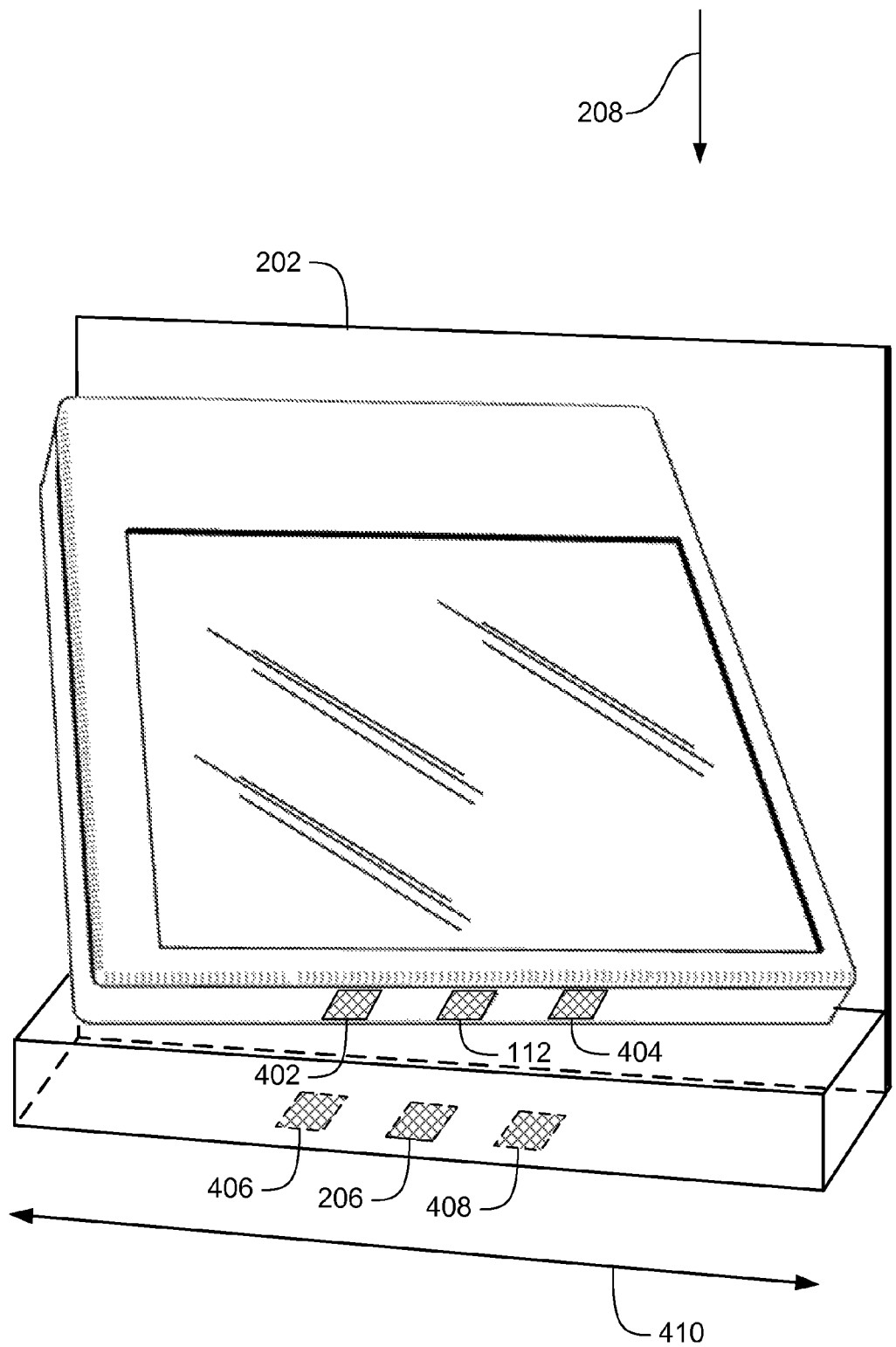
FIG. 4 is an isometric diagram of a portable wireless digital X-ray detector system and a docking detector receptacle having a plurality of three electrical conductors.

FIG. 4 is an isometric diagram of a portable wireless digital X-ray detector system and a docking detector receptacle having a plurality of three electrical conductors. The portable wireless digital X-ray detector system and docking detector receptacle of FIG. 4 provide a convenient means of providing power to the portable wireless digital X-ray detector from the docking detector receptacle.

Some implementations of portable wireless digital X-ray detector system 100 include a plurality of electrical conductors, such as the three electrical conductors 112, 402 and 404 shown in FIG. 4.

Some implementations of docking detector receptacle 200 include a plurality of electrical conductors, such as the three electrical conductors 206, 406 and 408 shown in FIG. 4. The electrical conductors 206, 406 and 408 and 112, 402 and 404 are positioned symmetrically along the longitudinal axis 410 so that electrical contact will be made between the docking detector receptacle 200 and the portable wireless digital X-ray detector system 100 regardless of whether the portable wireless digital X-ray detector system 100 is placed in the pocket 204 of the docking detector receptacle 200 with the panel 106 of the portable wireless digital X-ray detector system 106 facing the backplane 202 of the docking detector receptacle 200 or whether the portable wireless digital X-ray detector system 100 is placed in the pocket 204 of the docking detector receptacle 200 with the panel 106 facing out from the portable wireless digital X-ray detector 200.

Figure 5:
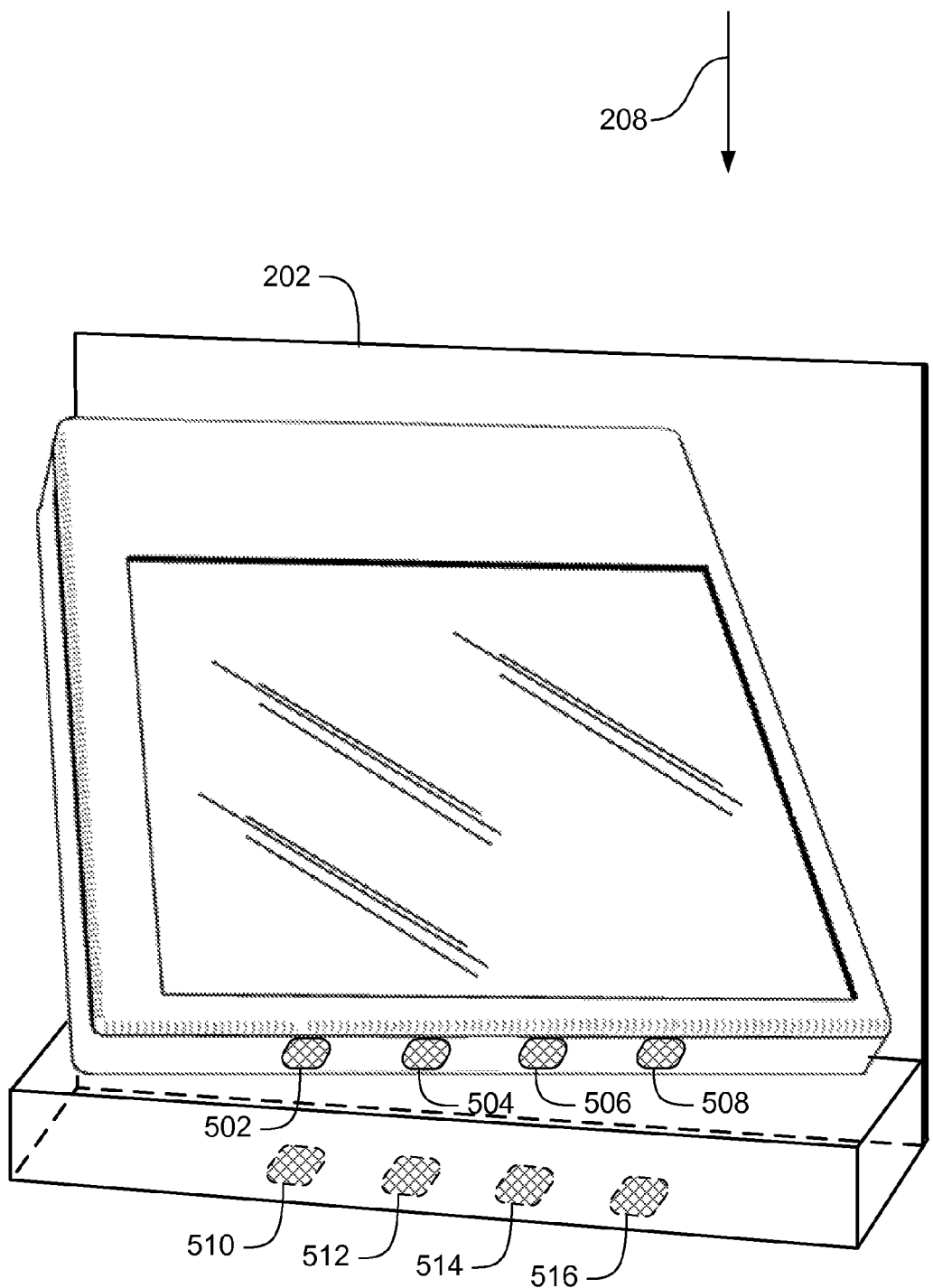
FIG. 5 is an isometric diagram of a portable wireless digital X-ray detector system and a docking detector receptacle having a plurality of four electrical conductors and/or electrical conductors having rounded corners.

FIG. 5 is an isometric diagram of a portable wireless digital X-ray detector system 500 and a docking detector receptacle 200 having a plurality of four electrical conductors and/or electrical conductors having rounded corners. The portable wireless digital X-ray detector system and docking detector receptacle of FIG. 5 provide a convenient means of providing power to the portable wireless digital X-ray detector from the docking detector receptacle.

Some implementations of portable wireless digital X-ray detector system 100 include a plurality of electrical conductors, such as the four electrical conductors 502, 504, 506 and 508 shown in FIG. 5.

In some implementations, the electrical conductors 502, 504, 506 and/or 508 have rounded corner(s). The rounded corner(s) of the electrical conductors 502, 504, 506 and/or 508 is particularly beneficial to a portable wireless digital X-ray detector system 500 that may come in contact with a patient, or person, because the rounded corner(s) reduce, if not eliminates, the possibility of the corner(s) of the electrical conductors 502, 504, 506 and/or 508 catching on the skin or clothing of patients or other people such as radiological technicians, nurses or physicians, and possibly causing injury to the person or possibly acting as a deposit of human epidermis and/or blood that could be passed to the next person who comes in contact with the electrical conductors 502, 504, 506 and/or 508, thus acting as a medium through which viruses and/or bacteria is transmitted from one person to another. Thus, the rounded corner(s) of the electrical conductors 502, 504, 506 and/or 508 prevents cross-contamination between people who have physical contact with the portable wireless digital X-ray detector system 500. In some implementations, the rounded corner(s) of the electrical conductors 502, 504, 506 and/or 508 are rounded to the extent that the electrical conductors 502, 504, 506 and/or 508 are circular in geometry. In some implementations, all of the corners of the electrical conductors 502, 504, 506 and/or 508 are rounded.

In some implementations, the electrical conductors 510, 512, 514 and/or 516 have rounded corner(s). The rounded corner(s) of the electrical conductors 510, 512, 514 and/or 516 reduces the likelihood of the corners catching on a portion of a portable wireless digital X-ray detector system when the portable wireless digital X-ray detector system is placed in the pocket of the docking detector receptacle 200. In some implementations, the rounded corner(s) of the electrical conductors 510, 512, 514 and/or 516 are rounded to the extent that the electrical conductors 510, 512, 514 and/or 516 are circular in geometry. In some implementations, all of the corners of the electrical conductors 510, 512, 514 and/or 516 are rounded.

In some implementations, the electrical conductors 510, 512, 514 and/or 516 have beveled edge(s) (not shown). The beveled corner(s) of the electrical conductors 510, 512, 514 and/or 516 reduces the likelihood of the edges catching on a portion of a portable wireless digital X-ray detector system when the portable wireless digital X-ray detector system is placed in the pocket of the docking detector receptacle 200.

In all of the portable wireless digital X-ray detector systems 100, 200, 300, 400 and 500 that have a plurality of electrical conductors, the electrical conductors have redundancy because of the multiple electrical conductors. The redundant electrical conductors decreases the likelihood that none of the plurality of electrical conductors are operable, such as caused by the electrical conductors being covered by non-conductive particles (e.g. dust). The decreased likelihood that all of the plurality of electrical conductors are inoperable at any given time, increases the likelihood that at least one of the electrical conductors will be operable at that time, thus improving reliability of the portable wireless digital X-ray detector systems 100, 200, 300, 400 and 500.

FIG. 6 is a cross section block diagram of an electrical conductor spring assembly 600. Spring 600 is one implementation of a spring that can be located underneath an electrical conductor of a docking detector receptacle, such as electrical conductor 206, to provide an outward force on the electrical conductor that will improve contact between the electrical conductor and an electrical conductor on a portable wireless digital X-ray detector system, thus improving electrical contact between the docking detector receptacle and the portable wireless digital X-ray detector system.

In the example of electrical conductor spring assembly 600, the electrical conductor is a pin 602, an apparatus having a cylindrical geometry with a flange 604 that holds the pin 602 under the interior surface 606 of the pocket of the docking detector receptacle. A spring 608 provides a tension force on the pin 602 that hold the pin 602 above flush over the interior surface 606 of the pocket of the docking detector receptacle when no force is applied against the pin 602. The spring 608 also has a tension force that holds the pin 602 about flush to the interior of the pocket 204 when a full weight of a portable wireless digital X-ray detector is applied against the pin 602.

Figure 7:
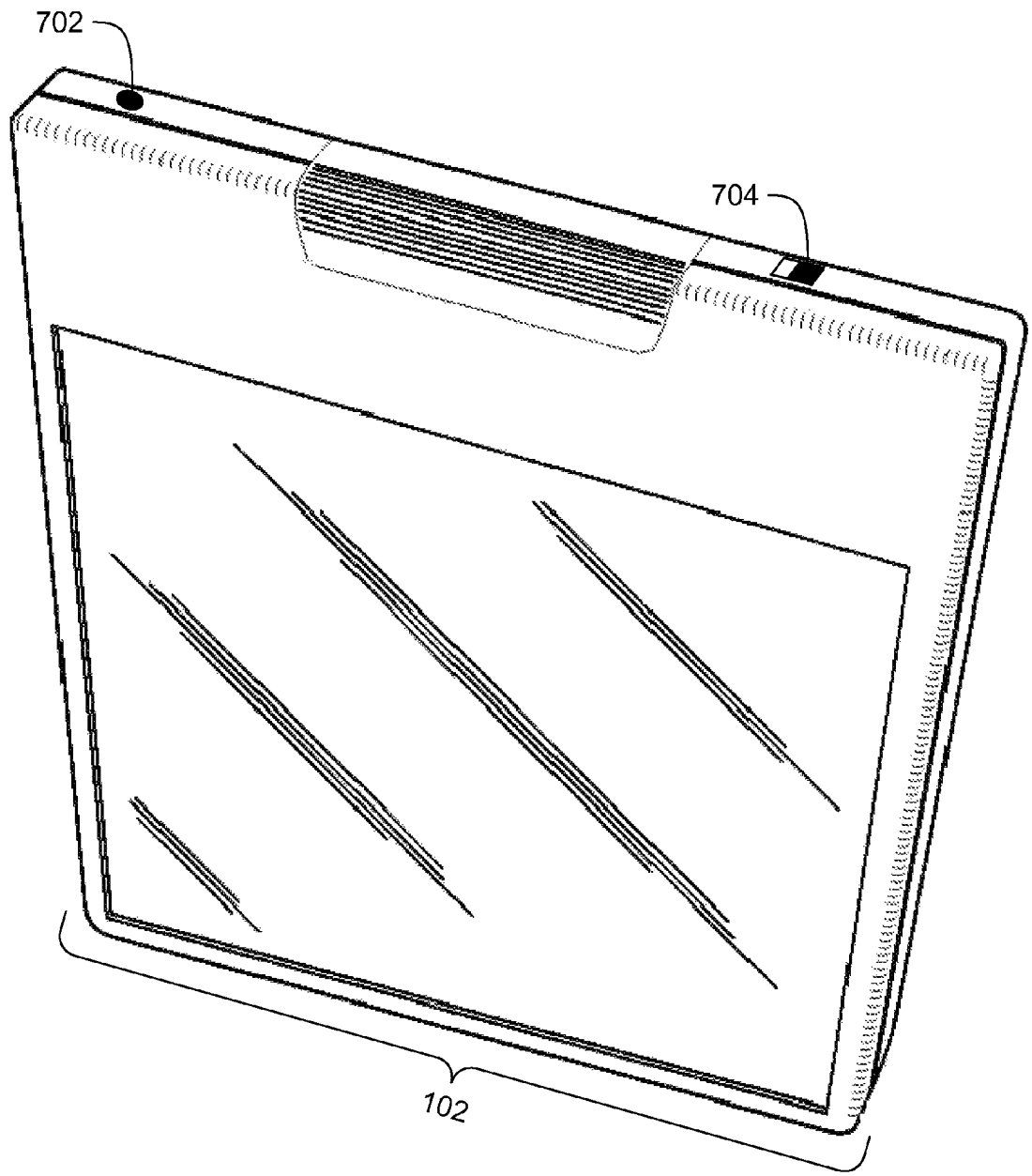
FIG. 7 is an isometric diagram of a portable wireless digital X-ray detector system having a battery-charging indicator and/or a battery-status indicator.

FIG. 7 is an isometric diagram of a portable wireless digital X-ray detector system 700 having a battery-charging indicator and/or a battery-status indicator.

Some implementations of the portable wireless digital X-ray detector system 700 include a battery-charging indicator 702. The battery-charging indicator 702 is operable to indicate two charging states of a battery, such as battery 110 in FIG. 1. The two states are "charging" and "not charging" to indicate whether or not the battery is being recharged. The battery-charging indicator 702 can be a light, such as a low power light-emitting diode (LED) in which a lighted condition of the light indicates that charging of the battery is occurring and an unlighted condition of the light indicates that charging of the battery is not occurring. The battery-charging indicator is mounted on the housing 102 and the battery-charging indicator 702 is operably coupled to the processor. In some implementations as shown in FIG. 7, the battery-charging indicator 702 is mounted on the top 702 of the housing 102 in order to be readily visible when the portable wireless digital X-ray detector system 700 is placed in a pocket of a docking detector receptacle, such as pocket 204 of docking detector receptacle 200. In some implementations (not shown), the battery-charging indicator 702 is mounted on a side 702 of the housing 102. In some implementations, the battery-charging indicator 702 is a speaker that enunciates a tone when the battery charge level is below a particular threshold.

Some implementations of the portable wireless digital X-ray detector system 700 include a battery-status indicator 704. The battery-status indicator 704 is operable to indicate an amount of charge of the battery, such as battery 110 in FIG. 1. In some implementations, the battery-status indicator 704 indicates which portion of a full-charge of the battery is charged. For example, the entire battery-status indicator 704 is fully lighted to indicate that the battery is fully charged, the battery-status indicator 704 is completely unlighted to indicate that the battery has no charge, and the battery-status indicator 704 is lighted halfway to indicate that the battery has 50% of a full-charge. In implementations where the battery-status indicator 704 is a light, such as a LED light, the LED is fully-lighted to indicate a full-charge in the battery, the LED is unlighted to indicate no charge in the battery, and the LED is half-lighted to indicate a 50% charge in the battery. In implementations where the battery-status indicator 704 is a contiguous series of lights, such as a series of LED lights, all of the LEDs are lighted to indicate a full-charge in the battery, none of the LED are lighted to indicate no charge in the battery, and half of the LEDs are lighted to indicate a 50% charge in the battery. In some implementations, the battery-status indicator 704 is a speaker that enunciates a tone when the battery charge level is below a particular threshold. In some implementations, and notice of low battery charge is provided through at least two levels. For example, at one level, when the remaining battery power is below a specific level (e.g. 5%), a warning is provided by the portable wireless digital X-ray detector system to the operator by means, for example, audio (a particular tone from detector or system) and and/or video (LED flash on detector and popup window on the screen of the system. For example at another level, when the remaining battery power is below a $2^{nd}$ level (e.g. 2%), the portable wireless digital X-ray detector system is powered off when the detector is not in the process of acquiring an image. Power off is delayed during image acquisition because emitting X-ray energy into a patient without obtaining an image is a safety concern to the patient.

The battery-status indicator 704 is mounted on the housing 102 and the battery-status indicator 704 is operably coupled to the processor. In some implementations as shown in FIG. 7, the battery-status indicator 704 is mounted on the top 704 of the housing 102 in order to be readily visible when the portable wireless digital X-ray detector system 700 is placed in a pocket of a docking detector receptacle, such as pocket 204 of docking detector receptacle 200. In some implementations (not shown), the battery-status indicator 704 is mounted on a side 704 of the housing 102.

Figure 8:
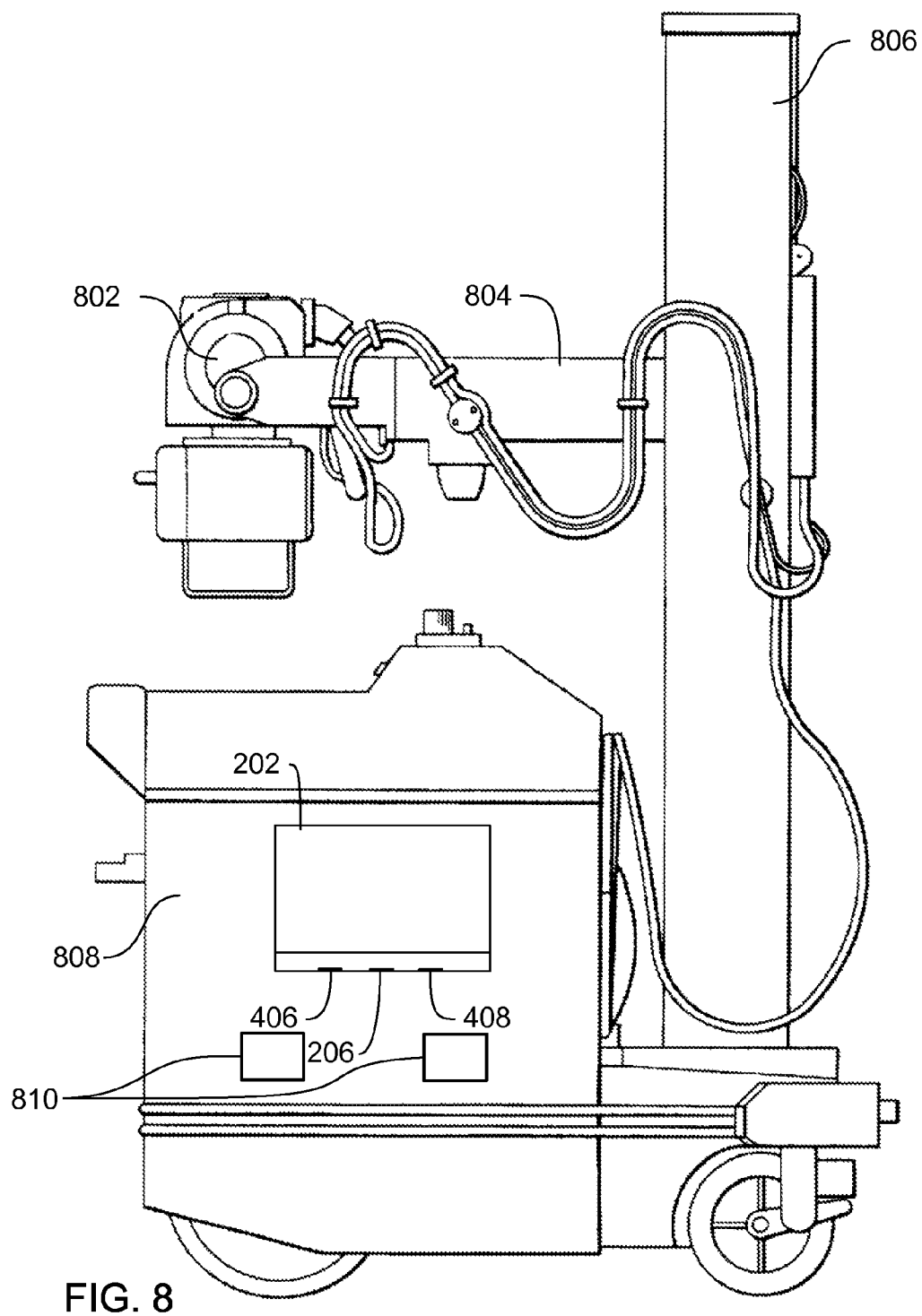
FIG. 8 is a side view of mobile digital X-ray imaging system according to an embodiment having one or more docking detector receptacles.

FIG. 8 is a side view of mobile digital X-ray imaging system 800 according to an embodiment having one or more docking detector receptacles. Mobile digital X-ray imaging system 800 includes an X-ray source 802 that is mounted to the end of a horizontal arm 804. The X-ray source 802 is positionable over an area of concern on a patient. The X-ray source 802 is typically mounted through a gimbal type arrangement in which a column 806 rotates to move the X-ray source from the park position on the mobile X-ray unit base 808 to the appropriate position in order to take an X-ray image of the patient.

Mobile digital X-ray imaging system 800 also includes one or more network adapters 812. Two network adapters in the plurality of network adaptors 812 are shown in FIG. 8, but any number of network adapters can be implemented. In implementations where two or more network adapters 812 is included, one of the network adapters 812 is used to connect to an external digital X-ray detector. One of the other additional network adapters 812 is used as an interface to an electronic system such as a picture archiving and communication systems (PACS) station that is operable to display an image from the mobile digital X-ray imaging system 800. At least one of the network adapters 812 is a conventional network adapter, such as an Ethernet adapter or universal serial bus (USB) adapter. USB is standard is published by the USB Implementers Forum, Inc. at 5440 SW Westgate Dr., Portland, Oreg. 94221.

Mobile digital X-ray imaging system 800 also includes one or more docking detector receptacles, such as the docking detector receptacle shown in FIG. 4. In FIG. 8, the docking detector receptacle is mounted on the side of the mobile digital X-ray imaging system 800, such as on the back of the mobile digital X-ray imaging system 800.

Mobile digital X-ray imaging system 800 network adapters 810 are operably coupled to the docking detector receptacle through a wired and/or a wireless communication link (not shown). The communication link provides a communication path between the docking detector receptacle and the mobile digital X-ray imaging system 800 electronic system that is operable to display an image from the mobile digital X-ray imaging system 800. Thus, information from a portable digital X-ray detector can still be transmitted from the portable digital X-ray detector when the portable digital X-ray detector is docked in the pocket 204 of the docking detector receptacle 400, through an electrical interface of the docking detector receptacle 400, such as electrical interface 512, to the electronic system that is operable to display an image.

Figure 9:
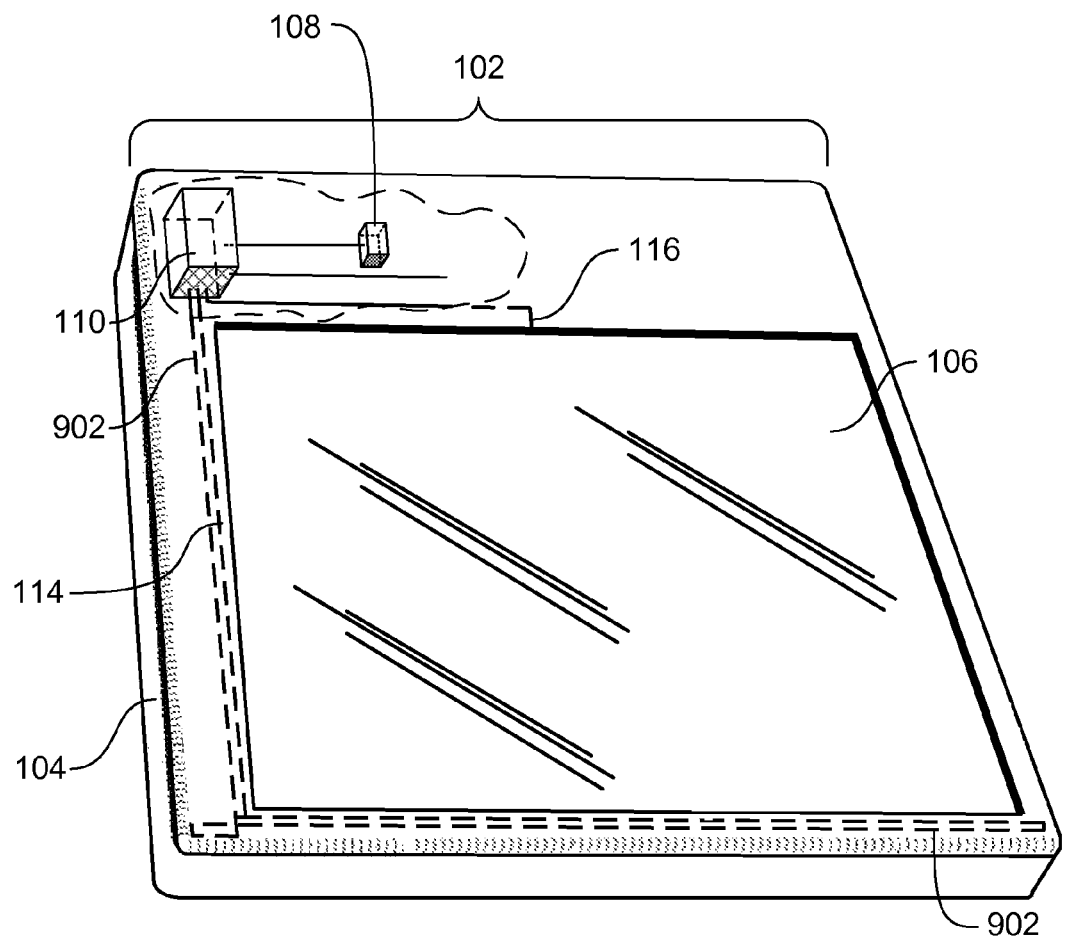
FIG. 9 is an isometric diagram of a portable wireless digital X-ray detector system having a non-contact inductive electrical supply module.

FIG. 9 is an isometric diagram of a portable wireless digital X-ray detector system 900 having a non-contact inductive electrical supply module. Some implementations of portable wireless digital X-ray detector system 900 include at least one non-contact inductive charging coil 902. The non-contact inductive charging coil 902 receives electromagnetic energy and converts the electromagnetic energy to electrical energy. The electrical energy is then used to charge the battery 110. In some implementations, the non-contact inductive charging coil 902 includes an induction module to receive the electromagnetic energy, a rectification module coupled to the induction module to rectify electric current from the induction module and a filter module to filter the rectified current from the rectification module. In some implementation, the non-contact inductive charging coil 902 replaces the electrical conductor(s) 112 (e.g. electrical conductor(s) 112 in FIG. 1) in which case, the portable wireless digital X-ray detector system 900 does not have electrical conductor(s). In some implementations not shown, the portable wireless digital X-ray detector system 900 includes the non-contact inductive charging coil 902 and the electrical conductor(s) 112. The non-contact inductive charging coil 902 requires no electrical conductor(s), provides uniform detector housing surface and is dust and water proof. In the implementation shown in FIG. 9, the non-contact inductive charging coil 902 is an electromagnetic coil that is wrapped around the housing 104 in the bottom area of the portable wireless digital X-ray detector system 900. The axis of the non-contact inductive charging coil 902 is oriented so that when the portable wireless digital X-ray detector system 900 is placed in the pocket 204 of the docking detector receptacle 1000 having an electromagnetic inductor, the coil 902 is aligned along the same axis as the electromagnetic inductor 1002 of the docking detector receptacle 1000 having an electromagnetic inductor.

Figure 10:
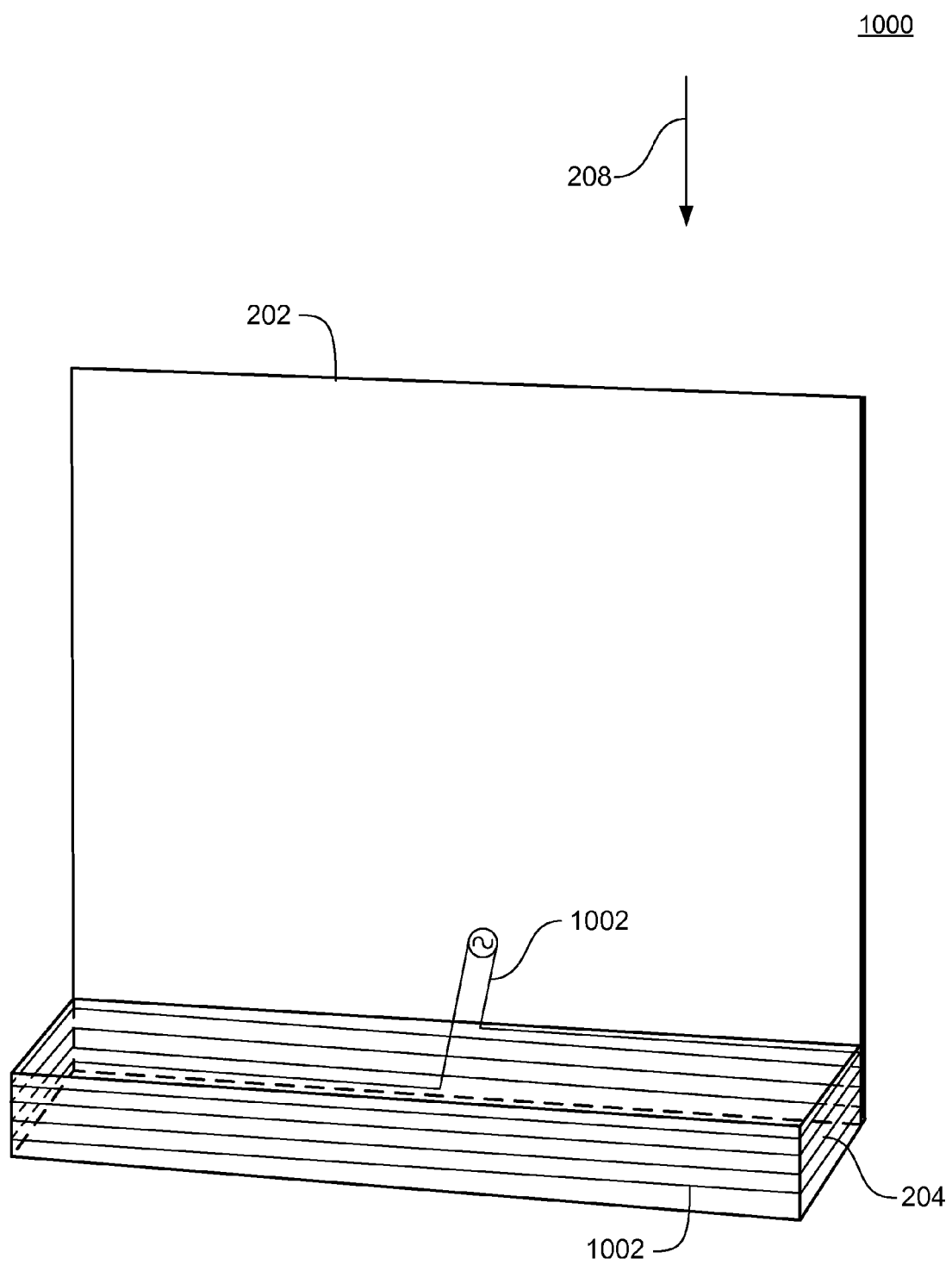
FIG. 10 is an isometric diagram of a docking detector receptacle having an electromagnetic inductor.

FIG. 10 is an isometric diagram of a docking detector receptacle 1000 having an electromagnetic inductor. Docking detector receptacle 1000 provides a convenient means of providing power to portable wireless digital X-ray detector that have a non-contact inductive charging module, such as a non-contact inductive charging coil 902 in FIG. 9. In FIG. 10 an electromagnetic inductor 1002 is operable to generate electromagnetic energy. In some implementations, the electromagnetic inductor 1002 is an electromagnetic coil. In other implementations not shown, the electromagnetic inductor 1002 is located in a mobile digital X-ray imaging system, such as mobile digital X-ray imaging system 800 in FIG. 8. In the implementation shown in FIG. 10, the electromagnetic inductor 1002 is an electromagnetic coil that is placed throughout a large area of the pocket 204 of the docking detector receptacle 1000 to improve transmission of electromagnetic energy. The axis of the electromagnetic inductor 1002 is oriented so that when the portable wireless digital X-ray detector system 900 is placed in the pocket 204 of the docking detector receptacle 1000, the coil 902 is aligned along the same axis as the electromagnetic inductor 1002 of the docking detector receptacle 1000.

Conclusion

A docking detector receptacle and portable wireless digital X-ray detector system having external electrical conductors is described. A technical effect of the docking detector receptacle and portable wireless digital X-ray detector system having external electrical conductors is electrical charging of a battery in the portable wireless digital X-ray detector system from the docking detector receptacle. Although specific implementations are illustrated and described herein, it will be appreciated by those of ordinary skill in the art that any arrangement which is calculated to achieve the same purpose may be substituted for the specific implementations shown. This application is intended to cover any adaptations or variations.

In particular, one of skill in the art will readily appreciate that the names of the methods and apparatus are not intended to limit implementations. Furthermore, additional methods and apparatus can be added to the components, functions can be rearranged among the components, and new components to correspond to future enhancements and physical devices used in implementations can be introduced without departing from the scope of implementations. One of skill in the art will readily recognize that implementations are applicable to future docking detector receptacles and new portable wireless digital X-ray detector systems. The terminology used in this application is meant to include all docking detector receptacles and new portable wireless digital X-ray detector systems and alternate technologies which provide the same functionality as described herein

We claim:

1. An apparatus comprising:
   a housing having an inside and an outside;
   a pixel array panel mounted inside the housing;
   a plurality of electronic components operably coupled to the panel;
   a battery electrically coupled to the plurality of electronic components and the panel;
   at least one electrical conductor having beveled edges and mounted flush within a tolerance of .01 millimeter to the outside of the housing, wherein each of the at least one electrical conductor comprises only hypoallergenic materials;
   a cover that spans each of the at least one electrical conductor,
   wherein the at least one electrical conductor is located on the housing in a position that is adjacent to a mating electrical conductor in a pocket of a docking detector receptacle when the apparatus is placed in the docking detector receptacle.

2. The apparatus of claim 1, wherein the at least one electrical conductor is a plurality of electrical conductors.

3. The apparatus of claim 2, wherein the plurality of electrical conductors are positioned symmetrically along a longitudinal axis of the apparatus.

4. The apparatus of claim 1, wherein the at least one electrical conductor is an electrically conductive plate located on a side on the outside of the housing.

5. The apparatus of claim 1, wherein the at least one electrical conductor is an electrically conductive pin located on a side on the outside of the housing.

6. The apparatus of claim 1 further comprising:
   a battery-status indicator that is operable to provide an audio indication of a status of the battery.

7. The apparatus of claim 1 further comprising:
   a battery-status indicator that is operable to provide a visual indication of a status of the battery.

8. The apparatus of claim 1 further comprising:
   a battery-charging indicator that is operable to provide an audio indication of a charging status of the battery.

9. The apparatus of claim 1 further comprising:
   a battery-charging indicator that is operable to provide a visual indication of a charging status of the battery.

10. The apparatus of claim 1, wherein the battery is removable.

11. A portable wireless digital X-ray detector comprising:
    a housing having an inside and an outside;
    a pixel array panel mounted inside the housing;
    a plurality of electronic components operably coupled to the panel;
    a battery mounted inside of the housing and electrically coupled to the plurality of electronic components and the panel; and
    at least one electrical conductor having beveled edges and mounted flush within a tolerance of .01 millimeter to the outside of the housing, wherein each of the at least one electrical conductor comprises only hypoallergenic materials;
    a cover that spans each of the at least one electrical conductor.

12. The portable wireless digital X-ray detector of claim 11 further comprising:
    at least one electrical conductor mounted flush to the outside of the housing.

13. The portable wireless digital X-ray detector of claim 12, wherein the at least one electrical conductor is a plurality of electrical conductors that are positioned symmetrically along a side of the housing.

14. The portable wireless digital X-ray detector of claim 11, wherein the battery is removable.

15. The portable wireless digital X-ray detector of claim 11 further comprising:
    at least one battery-status indicator.

16. The portable wireless digital X-ray detector of claim 11 further comprising:
    at least one battery-charging indicator.

17. An apparatus comprising:
    a back plane; and
    a pocket coupled to the back plane, the pocket having interior dimensions into which a portable digital X-ray detector fits and the pocket having at least one electrical conductor mounted to the interior of the pocket,
    wherein each of the at least one electrical conductor have beveled edges and are mounted flush within a tolerance of .01 millimeter to the outside of the pocket,
    wherein each of the at least one electrical conductor comprises only hypoallergenic materials.

18. The apparatus of claim 17, wherein the at least one electrical conductor is spring biased.

19. The apparatus of claim 17, wherein the at least one electrical conductor is a plurality of electrical conductors.

20. The apparatus of claim 19, wherein the plurality of electrical conductors are positioned symmetrically along a longitudinal axis of the apparatus.

21. The apparatus of claim 17, wherein the at least one electrical conductor is located on a bottom of the pocket.

22. The apparatus of claim 17, wherein the at least one electrical conductor is located on a side of the pocket.

* * * * *